United States Patent [19]

Buford, Jr. et al.

[11] 4,320,298

[45] Mar. 16, 1982

[54] WARHEAD DETECTOR

[75] Inventors: William H. Buford, Jr., Granada Hills; John J. Wagner, Woodland Hills, both of Calif.

[73] Assignee: The Marquardt Corporation, Van Nuys, Calif.

[21] Appl. No.: 190,830

[22] Filed: Apr. 27, 1962

[51] Int. Cl.² .............................................. G01N 23/00
[52] U.S. Cl. ................................ 250/358 R; 250/310;
250/390; 343/18 E
[58] Field of Search .............................. 343/100, 18 E;
250/83.1, 83.3, 83.6, 49.5, 84, 84.5, 83, 358, 369,
372, 484, 307, 303, 310, 390

[56] References Cited

U.S. PATENT DOCUMENTS

| | | | |
|---|---|---|---|
| 2,418,029 | 3/1947 | Hillier | 250/307 |
| 2,491,220 | 12/1949 | Segre | 250/390 |
| 2,952,775 | 9/1960 | Giunn | 250/336 |

Primary Examiner—Stephen C. Buczinski

EXEMPLARY CLAIM

1. Apparatus for the interception of an artificial earth orbiting satellite and the detection of thermonuclear material therein comprising, an interceptor vehicle having means for establishing and maintaining a given attitude in space with respect to said satellite, high-energy electron beam generating means carried within said vehicle, said attitude maintaining means being adapted to direct said electron beam toward said satellite and thereby produce bremsstrahlung from the interaction between said beam and the surface of said satellite, and neutron detector means carried within said vehicle and responsive to neutrons radiated from said satellite as a result of the interaction of said bremsstrahlung with thermonuclear material contained within said satellite.

3 Claims, 4 Drawing Figures

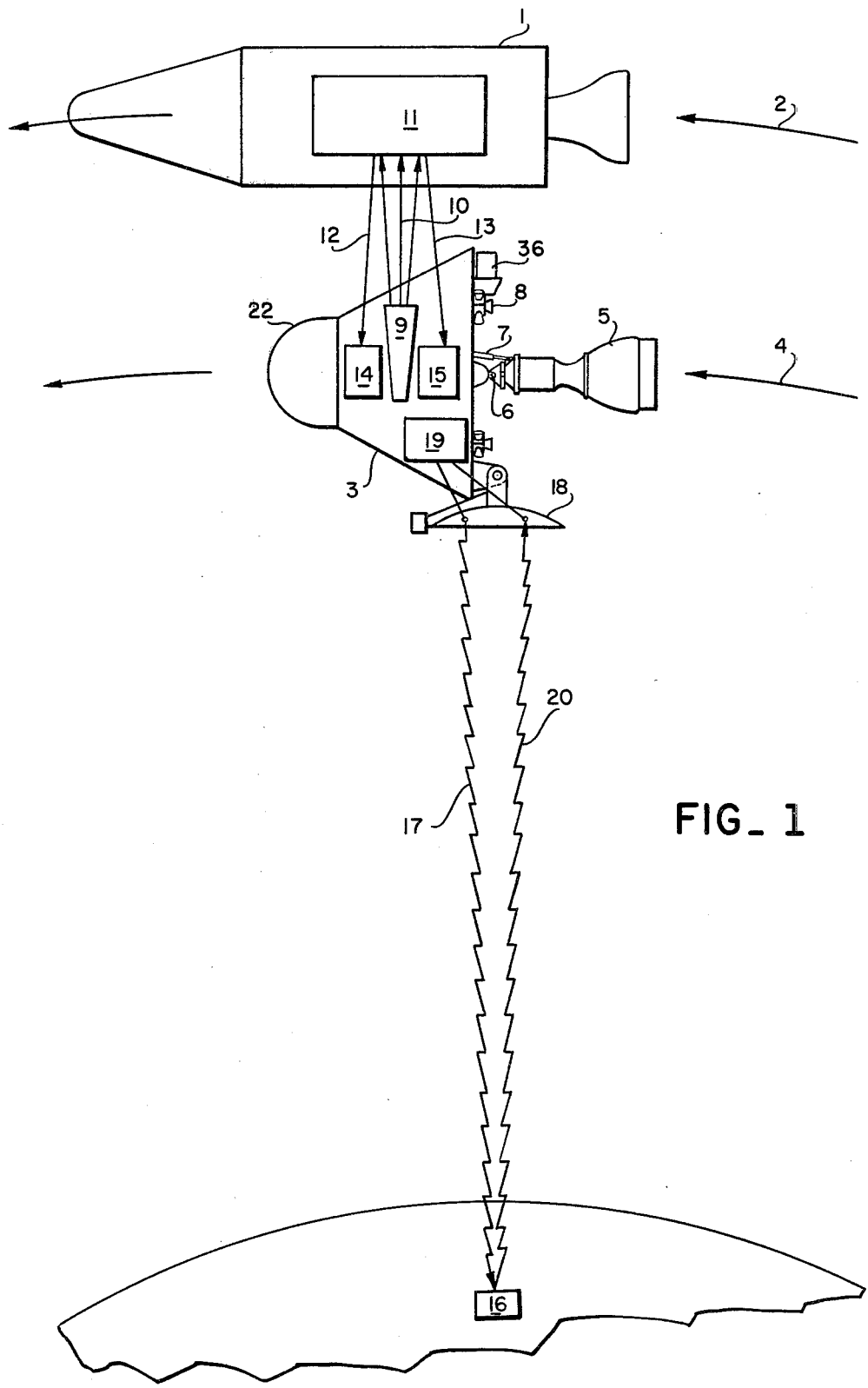
FIG_1

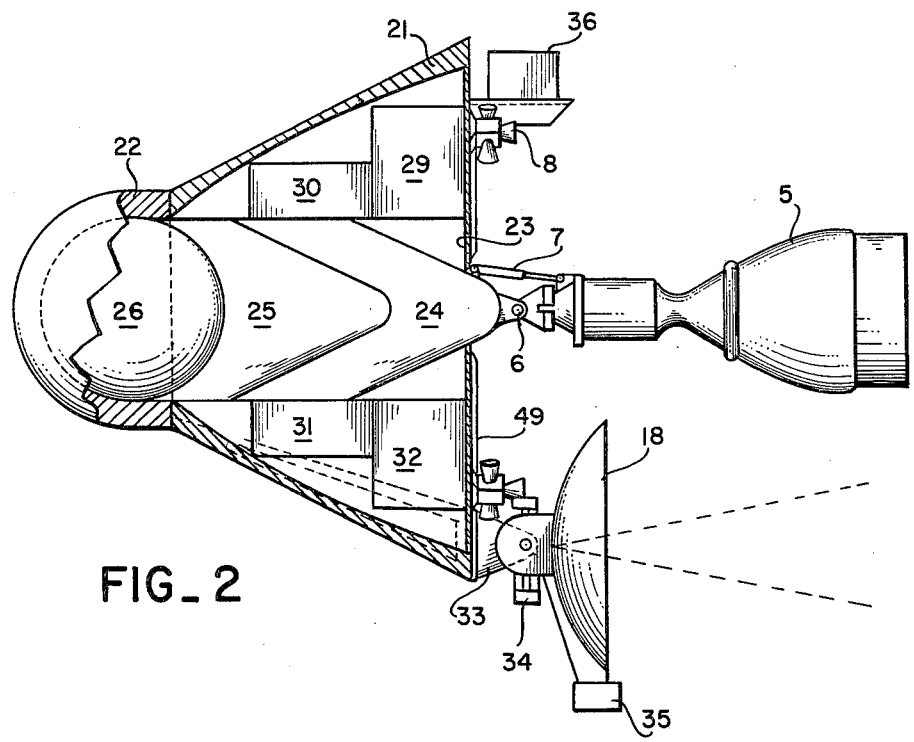
FIG_2
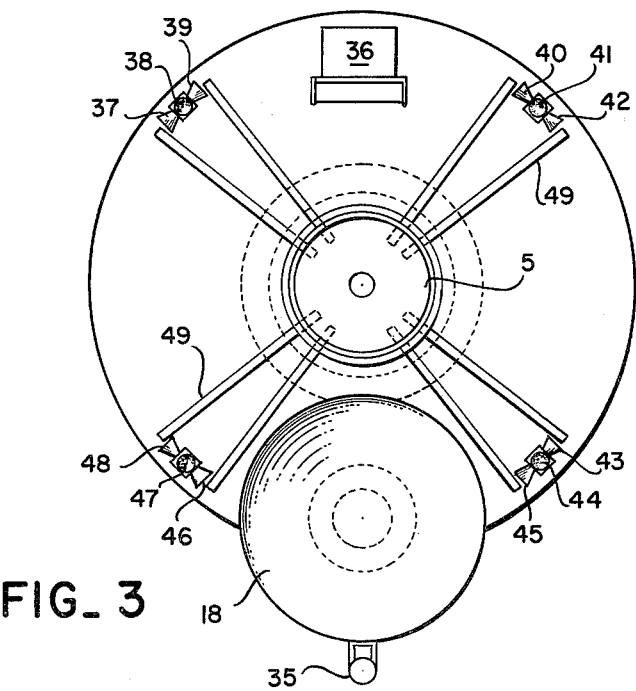
FIG_3

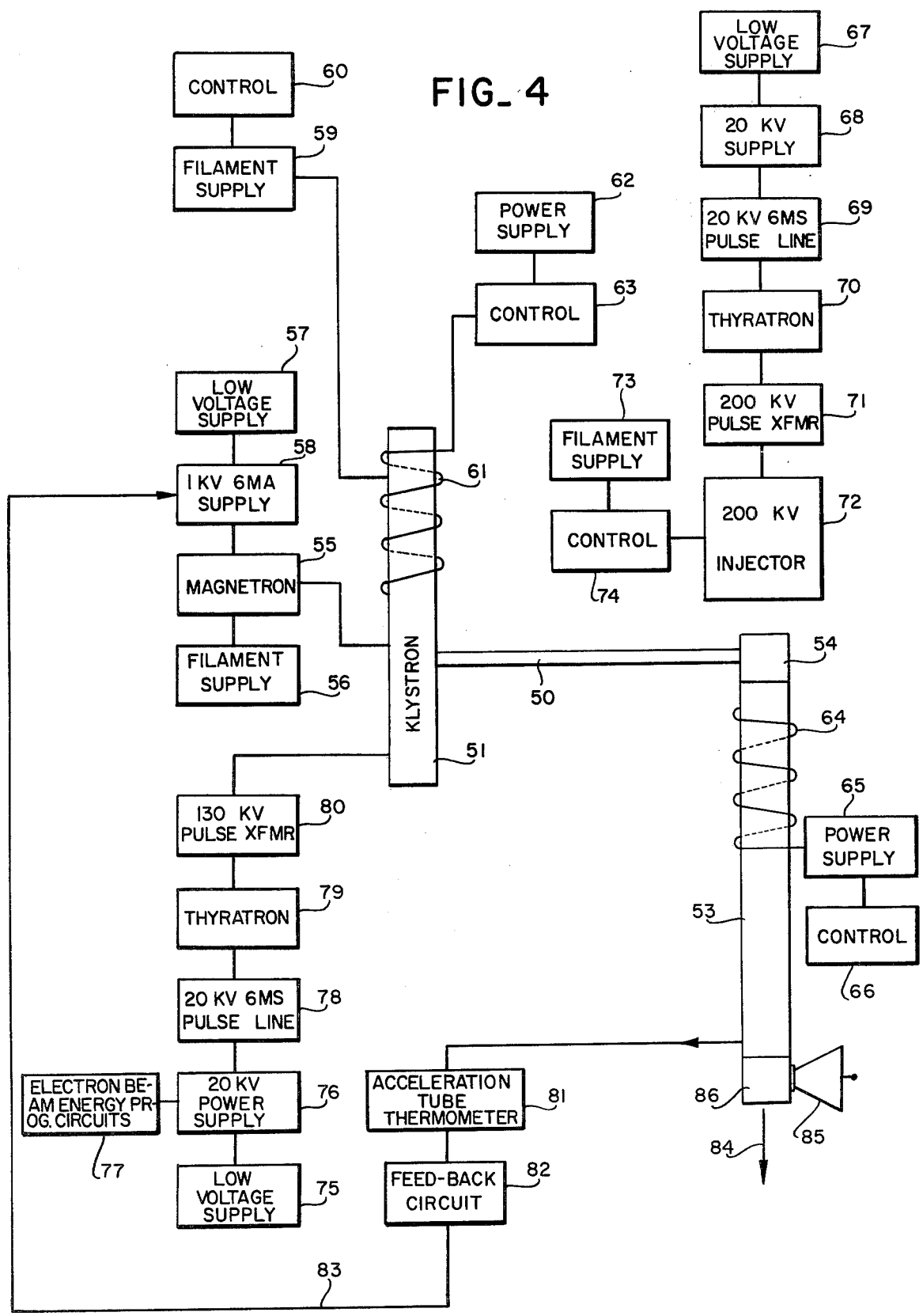
FIG_4

WARHEAD DETECTOR

This invention relates to a warhead detection system and more particularly to a detection system for ascertaining the presence of a thermonuclear warhead in a carrier vehicle such as a satellite.

The present invention is directed primarily to a detection system suitable for use in an interceptor satellite and inspection system to detect a thermonuclear warhead deployed in space. The interceptor satellite is designed to intercept an unknown satellite and, by internal detection means, determine whether the unknown satellite contains a thermonuclear warhead, without physically contacting the unknown satellite.

A constituent apparently common to all thermonuclear warheads is deuterium, usually in the form of lithium deuteride. Since it is considered extremely difficult, if not impossible, to build a thermonuclear warhead without deuterium, it becomes feasible to detect the presence of such a warhead by irradiation of the deuterium with high energy gamma rays which will result in the emission of fast neutrons (photoneutrons).

The proper selection of gamma ray energy will distinguish the deuterium from any other elements present. The photoneutrons produced by the gamma ray radiation can be counted by the interceptor inspection satellite and a positive decision as to the presence or absence of a thermonuclear warhead can be made.

While the invention will be described hereinafter as carried within an interceptor satellite vehicle, it should be understood that the detection apparatus may be contained within any suitable housing, fixed or mobile, for detection of thermonuclear warheads at any site.

The detection system comprises two major components namely, (1) a device to produce the gamma rays in the proper energy range and, (2) an accurate neutron detection and assessment system.

In a preferred embodiment the interceptor satellite contains an electron accelerator capable of delivering high intensity pulses of electrons at energies in the range of four to six million electron volts (Mev) to the intercepted satellite. The electrons from the accelerator are beamed to the surface of the intercepted satellite which serves as the target material for gamma ray production. Gamma rays (bremsstrahlung gamma rays) are produced by the interaction of the high energy electrons with the surface skin material of the intercepted satellite. The maximum gamma ray energy produced will equal the maximum electron energy of the electron beam. The control of the maximum gamma ray energy is essential to warhead detection.

The threshold for photoneutron production in deuterium is 2.32 Mev. The only other element capable of producing appreciable photoneutrons with relatively low gamma ray energys are: $Be^9$ ($E_T$=1.67 Mev), $C^{13}$ ($E_T$=4.9 Mev), and $Li^6$ ($E_T$=5.3 Mev). The use of a maximum gamma ray energy below the $C^{13}$ threshold absolutely eliminates response from all elements except $D^2$ and $Be^9$. A gamma ray energy near or below the $D^2$ threshold can then distinguish between $Be^9$ and $D^2$.

A warhead satellite can easily be disguised as any other type of satellite as far as external physical parameters are concerned. Thus, it becomes important that a positive detection technique for warhead threat assessment be made available.

Suspicious materials indicating a likelihood of a warhead are fissionable materials, tritium or deuterium. The fissionable materials will be present in both fission and thermonuclear warhead devices. Uranium 233, uranium 235, or plutonium 239 might be used; therefore, any detection technique must be able to detect any of the three possibilities. Fissionable materials will also be present in a reactor so that fissionable material detection alone will never positively identify a warhead.

Tritium may be present in both fission and fusion warhead devices; however, the amount present will be small and thus detection of tritium appears unlikely at the present state of the art. Deuterium will always be present in significant amounts in a thermonuclear device. Deuterium can be used as a moderator for a reactor, but its use in a space deployable reactor is unlikely. Yield-to-weight ratios make thermonuclear warhead deployment in space much more likely than fission warhead deployment. Deuterium detection in the satellite system gives a more positive indication of the presence of a warhead than does the detection of any of the other suspicious materials.

Photoneutrons produced by gamma ray interactions with warhead materials suffer many collisions, energy degradations, direction changes, etc.; however, relatively few are lost in leaving the warhead and satellite. The warhead satellite then appears very like an isotropic source of neutrons and the neutron intensity at typical interceptor satellite positions (50 to 500 feet) are easily measured with conventional neutron detection devices.

An electron current of $10^{15}$ electrons/second will produce a flux of 35 $n/cm^2$-sec at the inspection satellite located at a distance of 50 feet. Pulsing the electrons in a shorter time interval will produce an effective flux several orders of magnitude greater than this and flux measurements can be made even in the presence of intense background radiation.

The invention resides partly in the physical and electrical structures and inter-relationships embodied in the high energy electron source and photoneutron detection components of the system as herein specifically illustrated, but also embraces the concept of the system itself, considered as an integrated whole, and independently of the structural details of its several parts.

It is therefore, an object of this invention to provide a novel and improved device for detecting the presence of a thermonuclear warhead.

It is another object of the present invention to provide apparatus for discrimination between a warhead and a non-operating nuclear reactor.

Another object of the invention is to detect deuterium by means of the phenomenon of photoneutron production.

Yet another object of the invention is to provide novel and improved interceptor satellite apparatus for the inspection of suspect satellites deployed in space.

A general object of this invention is to provide new and improved detector apparatus which overcomes disadvantages of previous means and methods heretofore intended to accomplish generally similar purposes.

Many other advantages, features and additional objects of the present invention will become manifest to those versed in the art upon making reference to the detailed description and the accompanying sheets of drawings in which a preferred structural embodiment, incorporating the principles of the present invention is shown by way of illustrative example.

In the figures:

FIG. 1 is a diagrammatic representation of an interceptor satellite containing the detector apparatus of the invention, stationed in proximity to a suspect satellite.

FIG. 2 is an elevation view, partially in section, of the interceptor satellite apparatus of FIG. 1.

FIG. 3 is a rear elevation view of the apparatus of FIG. 2.

FIG. 4 is a schematic diagram of the electron accelerator apparatus useful in the practice of the invention.

While the useful application of the detector system of this invention need not be limited to a satellite vehicle carrying a thermonuclear warhead, for purposes of teaching the invention, this particular application will be described in detail.

Looking now at FIG. 1, there is shown a suspect satellite vehicle 1 orbiting the earth in the direction of arrow 2. For the purpose of determining whether satellite vehicle 1 carries a nuclear warhead, interceptor inspection satellite vehicle 3 is launched and maneuvered into an orbit close to that of vehicle 1 so that it will follow an orbital trajectory indicated by arrow 4.

As will be evident to those skilled in the art, any suitable launching vehicle may be employed to place vehicle 3 into the desired orbit. Typically, such a launching vehicle would comprise a multi-stage rocket with the last stage consisting of vehicle 3. Satellite 3 is propelled by rocket engine 5 which is mounted by means of a gimbal mechanism 6 having control linkages 7 for positioning engine 5 in a manner required for directing the vehicle 3 along the desired orbital path. Position attitude control is achieved by means of a plurality of vernier rocket motors, a typical one of which is shown at 8. These vernier rocket motors will provide the necessary yaw, pitch and roll correction necessary to maintain vehicle 3 in close proximity to vehicle 1 and suitably aligned with respect thereto, as will be seen hereinafter.

Linear accelerator 9 provides a high energy electron beam 10 which irradiates vehicle 1. By means of the attitude control vernier motors, satellite 3 may be positioned so that the electron beam is directed to the surface of the intercepted satellite 1. The skin of the suspect satellite 1 is used as the target material for the bremsstrahlung gamma ray production.

Accelerator 9 produces electrons to excite X-rays in the suspect satellite. The electron beam from accelerator 9 impinges directly on the suspect satellite and will produce bremsstrahlung photons which in turn will excite photoneutron production in the thermonuclear warhead material if a warhead is present.

Assuming that vehicle 1 contains a quantity of deuterium 11, neutrons will be radiated outwardly, some of which will be directed back toward vehicle 3 along the paths indicated at 12 and 13. These neutrons will be detected by neutron detectors 14 and 15. Interrogation by radio link 17 may be achieved from a ground station 16, which is picked up by antenna 18, and fed to receiver 19. The detected signals from neutron detectors 14 and 15 will be retransmitted via transceiver 19 and antenna 18 to ground station 16 via radio link 20.

The neutron detectors 14 and 15 may be of any suitable and well-known construction. For example, in a practical embodiment, high sensitivity boron trifluoride proportional counters of the type manufactured by Westinghouse Electric Corporation, and identified as their type WL-6938 may be employed. These neutron detectors each comprise a high sensitivity multielement proportional counter, designed to detect thermal and intermediate speed neutrons in the flux range from $2.2 \times 10^{-2}$ to $2.2 \times 10^3$ neutron/cm$^2$/second.

The use of boron trifluoride proportional counters for the detection of thermal neutrons depends upon the exothermic nuclear reaction $B^{10}$ $(n,\alpha)$ $Li_7$. The ionization resulting from the energy loss of the alpha particle and lithium nucleus in boron trifluoride gas is collected and gives rise to a pulse charge at the collecting electrode for each boron disintegration occuring in the counter.

These detectors utilize a polyethylene moderator block enclosed by a heavy-walled aluminum shield. These devices also employ $BF_3$ enriched to 96% in Boron-10 isotope as the neutron sensitive material resulting in an overall sensitivity of approximately 45 counts/neutron/cm$^2$ with an operating voltage of 2000 volts.

Looking now at FIG. 2, there is shown additional structural details of the interceptor vehicle 3. The inspection satellite vehicle comprises a main housing structure 21 to which is attached nose cone 22 and the rearward end is enclosed by panel 23. The engine 5 is carried by an articulated gimbal mechanism 6 carrying hydraulic cylinder 7 for controlling the attitude of engine 5 with respect to the vehicle housing 21.

Rocket fuel for engine 5 is carried within fuel tank 24 and oxidizer for the engine is carried within tank 25. Helium tank 26 provides a pressure source for propelling the fuel and oxidizer into the engine 5 and also for providing the pressurized gas for operating the vernier rocket motors, such as that indicated at 8.

The linear accelerator is contained within housing 29 and the neutron detectors are contained within housings 30 and 31. Transceiver apparatus is located at 32. By means of transceiver 32, control signals from the earth-based ground station 16 may be communicated to utilization circuits within the satellite, and also, signals detected by neutron detectors 30 and 31 may be transmitted to the earth-based station 16. Television signals, useful in controlling the attitude of the satellite are also transmitted to the earth-based station 16 by means of transceiver 32. Transceiver antenna 18 is pivotally mounted on bracket 33 and has a servo mechanism 34 which permits it to be oriented in such a manner that the antenna dish 18 may be directed toward the earth regardless of the attitude of vehicle 3. A television camera 35 is mounted on the antenna 18 and is coupled to the transmitter portion of transceiver apparatus 32.

By viewing the horizon via camera 35 and transmitting such video data to the earth, the attitude of the vehicle and antenna 18 will be made known to operating personnel. Also, a second television camera may be contained within housing 36 for viewing the unknown or intercepted satellite. Video data from this second camera are transmitted by means of transceiver 32, to which it is connected. Such data will, of course, be useful in maneuvering the inspection vehicle 3 in proximity to the intercepted vehicle 1. Guidance equipment also may be enclosed within housing 36.

The attitude control vernier rocket motors are more clearly shown in FIG. 3. In a typical practical embodiment there are a total of twelve motors arranged in clusters of three and disposed about the periphery of panel 23 as shown in FIG. 3. The three vernier motors in cluster are used to control yaw, pitch, and roll, respectively. These motors are identified in FIG. 3 as 37–48. Panel 23 carries a plurality of stiffening ribs, a typical one of which is shown at 49.

The disclosure given up to this point is intended only to explain the fundamental arrangement of the warhead detector apparatus as carried within the terminal vehicle of an interceptor satellite system without enumerating all structural details of the vehicle apparatus.

As will be apparent to those skilled in the art, various modifications in the engine, propellant tanks and attitude control system may be made. The general configuration shown is considered to be sufficient to enable those skilled in the art to practice the invention. The general configuration is preferred in order to avoid difficult dynamic control problems. For example, it is necessary to cluster the propellant tanks 24-25 about the thrust axis in a manner which allows the center of gravity shift to be along the thrust axis with a minimum transverse shift. The hopper-bottom tanks (24 and 25) shown are preferred since they minimize fuel sloshing problems. The control vernier motors 37-48 are mounted in a position which allows pitch and yaw without translation and, in addition, pure translation.

The forward end of this conical structure is formed by the helium pressurization tank 26 and the propellant tanks 24 and 25 both assembled as an integral unit. The detection equipment cavity is formed between the tanks 24 and 25, the housing 21, and the control motor mounting panel 23.

Looking now at FIG. 4, there is shown a block diagram of the linear accelerator portion of the detector apparatus. Inasmuch as each of the functional units represented by a rectangle in the diagram may be any one of the number of devices for each representative function, well known in the art, it is deemed unnecessary to show circuit details. The system shown is described in sufficient detail to enable those skilled in the art to practice it.

Any suitable source of high energy electrons may be employed; however, there is shown, by way of example, in FIG. 3, typical linear accelerator of suitable characteristics and capable of furnishing an appropriate number of 5 Mev electrons. Briefly, the principle of operation is as follows: The electron linear accelerator comprises a waveguide 50 which is supplied with short duration, high-power pulses of RF energy, generated by magnetron 55 and amplified by klystron 51 as in radar play. Typically the apparatus uses radar power components, which may, for example, be of the "S" band type.

A traveling wave of the proper phase velocity is propogated via waveguide 50 into accelerator tube 53. Electrons are injected via coupler 54 at the proper intervals to be trapped in the field of the traveling wave and to be accelerated in tube 53. Inasmuch as the device is deployed in space, operating power is obtained from batteries.

In a preferred embodiment, the batteries are of the silver-zinc type, storing 10 to 40 watt hours per pound.

The RF energy is generated by magnetron 55 which in turn drives klystron 51. Batteries comprise the filament supply 56 for magnetron 55. A battery powered supply 57 energizes the 1 kilovolt (KV) supply 58 for operating magnetron 55. Filament power for klystron 51 is obtained from filament battery 59 and is regulated by suitable control means 60. The focus coils 61 for klystron 51 are energized from a battery power supply 62 and regulated by any suitable control means 63. Focus coils 64 for accelerator tube 53 are powered from battery supply 65 which is regulated by control means 66.

A low-voltage battery power supply 67 energizes 20 KV supply 68 which energizes a 20 KV, 6 microsecond pulse line 69. The pulse output from 69 is switched by thyratron 70 which energizes the 200 KV pulse transformer 71. The 200 KV pulses are injected into tube 53 via coupler 54 by means of injector 72. Filament battery 73 is regulated by control means 74 and supplies filament power to injector 72.

The prime power supply for klystron 51 is derived from a low-voltage battery supply 75, which in turn energizes 20 KV power supply 76. Electron beam energy programming circuits 77 control the power supply to the RF power klystron 51. The 20 KV, 6 microsecond pulse line 78, thyratron 79, and the 130 KV pulse transformer 80, supply the high-energy pulses required for the operation of klystron 51. The 20 KV power supplies 68 and 76 are approximately 50 percent wasted and deliver 50 watts per pound. Because of the short duty cycle of the equipment, no cooling system need be provided.

However, some provision must be made for dimensional changes in the accelerator arising from temperature variations. Thus, to prevent serious detuning of the accelerator, feed back is used to control the RF frequency in accordance with accelerator tube 53 temperature. This feed-back circuit comprises acceleration tube thermometer 81 and feed-back circuit 82 which supplies the necessary correction signal on line 83 to the magnetron power supply 58.

A horn antenna 85, coupled to tube 53 via coupler 86, is used to dissipate waste RF energy. The 5 Mev x-rays emerge in a beam as indicated by arrow 84. The apparatus described is capable of producing $10^{14}$ electrons at 5 Mev in 30 pulses, each 5 microseconds long (100 milliampere peak pulse current). In a typical operation, satellite inspection time is approximately one minute. Operating the accelerator at 30 pulses per second, and with the detector system described hereinabove, a warhead may receive between 20 and 90 individual "observations", and remain within the power supply capabilities of a practical system.

The irradiation of a target satellite with a beam of electrons in the space environment presents problems of satellite charge neutralization. The interceptor satellite repeatedly builds up a positive charge during the electron irradiation when no neutralization technique is provided. During the course of several "observations" the electron energy could be seriously degenerated from the desired 5.0 Mev level, due to the satellite charge build-up. However, the total ion transfer from satellite to satellite is quite small. This permits the use of a small plasma source aboard the interceptor satellite to provide sufficient neutralization during the irradiation.

As has been mentioned hereinabove, the detector apparatus need not be carried within a space vehicle, but may also find useful application in detecting nuclear warheads in land vehicles, ships, etc. Regardless of the means of bringing the detection apparatus into proximity with the suspect warhead carrier, the apparatus radiates photons of energy between 2.3 and 5 Mev and the resulting generation and detection of thermal and intermediate speed neutrons is indicative of the presence of deuterium or beryllium. Beryllium discrimination can be achieved, if necessary, by selecting the photon energy. In the preferred embodiment the electron energy in the accelerator has been selected as 5 Mev.

The principal application of the invention is in the detection of deuterium as a constituent of thermonuclear warheads. However, the apparatus of the invention is also useful in detecting the presence of fissionable materials such as uranium or plutonium. This is achieved by exciting and detecting the characteristic x-ray (K or L) of uranium or plutonium. As in the case in which the apparatus is used to detect deuterium, high-energy electrons are caused to strike the skin of the warhead and thus produce bremsstrahlung photons; these, in turn, will excite the characteristic x-ray in the fissionable materials if they are present. The sensitivity of the radiation counter or detector will be selected to be responsive to the characteristic K line of uranium, or the characteristic L line of plutonium. The basic structure of the apparatus would otherwise be the same as that described in detail hereinabove.

Thus, there has been described and shown novel and improved apparatus for detecting the presence of a thermonuclear warhead. Since certain changes may be made in the above method and apparatus, without departing from the scope of the invention herein involved, it is intended that all material contained in the above description or shown in the accompanying drawings shall be interpreted as illustrative and not in a limiting sense.

What is claimed is:

1. Apparatus for the interception of an artificial earth orbiting satellite and the detection of thermonuclear material therein comprising, an interceptor vehicle having means for establishing and maintaining a given attitude in space with respect to said satellite, high-energy electron beam generating means carried within said vehicle, said attitude maintaining means being adapted to direct said eletron beam toward said satellite and thereby produce bremsstrahlung from the interaction between said beam and the surface of said satellite, and neutron detector means carried within said vehicle and responsive to neutrons radiated from said satellite as a result of the interaction of said bremsstrahlung with thermonuclear material contained within said satellite.

2. Apparatus as defined in claim 1 having radio communication means contained within said vehicle for transmitting the output from said neutron detecting means, and a ground-based station for receiving said transmitted output.

3. The method of inspecting an artificial earth orbiting satellite in order to detect the presence of a thermonuclear warhead therein comprising the steps of maneuvering a rocket propelled interceptor vehicle into close proximity to said satellite, directing a beam of high-energy electrons from said vehicle to impinge on said satellite, and detecting thermal neutrons radiated from said satellite to indicate the presence of thermonuclear material therein.

* * * * *